United States Patent [19]

Sanchez, Jr.

[11] Patent Number: 5,477,871
[45] Date of Patent: Dec. 26, 1995

[54] DENTAL FLOSS RETAINER RING

[76] Inventor: Daniel Sanchez, Jr., 1837 W. Fulton, 3rd Fl., Chicago, Ill. 60612

[21] Appl. No.: 224,509

[22] Filed: Apr. 7, 1994

[51] Int. Cl.⁶ ................................................. A61C 15/00
[52] U.S. Cl. ............................................. 132/323; 132/324
[58] Field of Search .............................. 132/321, 323, 132/325, 326, 324, 327; 242/125.1, 125.2

[56] References Cited

U.S. PATENT DOCUMENTS

| | | |
|---|---|---|
| D. 323,722 | 2/1992 | Lott .............................................. D28/54 |
| 678,540 | 7/1901 | Chase ........................................ 242/125.2 |
| 2,086,272 | 7/1937 | Johl ........................................... 242/125.2 |
| 3,696,821 | 10/1972 | Adams, IV . |
| 3,901,251 | 8/1975 | Johnston . |
| 4,034,770 | 7/1977 | Trecker . |
| 4,254,786 | 3/1981 | Won .............................................. 132/325 |
| 4,638,824 | 1/1987 | De La Hoz . |
| 4,926,820 | 5/1990 | Wearn ........................................... 132/323 |
| 5,062,580 | 11/1991 | Meagher ..................................... 242/125.2 |
| 5,199,452 | 4/1993 | Cheng .......................................... 132/325 |
| 5,222,510 | 6/1993 | Zuehlsdorf ................................... 132/323 |

*Primary Examiner*—Cary E. O'Connor
*Attorney, Agent, or Firm*—Gerstman, Ellis & McMillin Ltd.

[57] ABSTRACT

A dental floss retainer ring is provided, having a size permitting placement on the finger. The ring defines circumferential sidewalls to form an external, annular space between the walls for receiving a winding of dental floss about the ring. One of the walls defines at least one slot extending only incompletely across the ring to facilitate the securance of a portion of dental floss as the dental floss is wound about the ring. The process of dental flossing teeth is facilitated by the use of one or a pair of such dental floss retainer rings.

8 Claims, 1 Drawing Sheet

DENTAL FLOSS RETAINER RING

BACKGROUND OF THE INVENTION

The majority of dentists recommend that the health of teeth can be greatly enhanced by the use of dental floss. However, the process of use is rather inconvenient and disagreeable, particularly because of the pressure that the thin dental floss exerts against the finger, sinking deep into the tissue, and being rather uncomfortable as the dental floss is forced by the fingers between the teeth.

Numerous designs of dental floss retainer devices have been proposed so that one does not have to wind the dental floss around the finger and have the dental floss dig into the tissue during use. However, none of the previously proposed designs have been truly satisfactory in use, nor have any of them achieved any significant commercial success.

By this invention, a simple, inexpensive dental floss winding ring is provided, the winding ring being carried on the finger to protect it as the dental floss is wound about it. Thus, the flossing process is facilitated in that one can freely wind and/or unwind the dental floss, loop by loop, from the ring, shifting the dental floss as one uses it to penetrate between the teeth, without the unpleasant digging of the dental floss into the tissue of the finger. Also the dental floss ring may be used to carry a substantial supply of dental floss for gradual unwinding during use, to achieve a more pleasant and effective use of the dental floss.

DESCRIPTION OF THE INVENTION

By this invention a dental floss retainer ring is provided, being of a size permitting placement on the finger. The ring is preferably sized to be loosely positionable on the finger for easy removal.

The ring defines circumferential sidewalls which define an external, annular space between the sidewalls for receiving a winding of dental floss about the ring. One of the walls defines at least one slot, which extends only incompletely across the ring, to facilitate the securance of an end portion of dental floss as the dental floss is wound about the ring.

It is preferable for the other wall to have no slot in a position that corresponds to the position of the one slot or slots. It is also preferred for the part of the retainer ring which is between the walls to be mostly free of any such corresponding slot. Typically, only the one wall carries slots, while the other wall and the remainder of the ring are slot free.

In one embodiment, one of the sidewalls can define a pair of the slots described above in closely spaced relation. These slots may extend substantially parallel to the nearest radius of the ring, for example a radius of the ring that passes between the pair of slots. Alternatively, the one slot defined in one of the sidewalls may extend substantially transversely to the nearest radius of the ring. Also, a pair of such transversely extending slots may be defined by the one sidewall in closely spaced relation.

Alternatively, a single slot may be provided in a relation extending substantially parallel to a ring radius that passes through it.

By this invention, the slot or slots which are present are used to help secure a forward portion of dental floss, so that further loops of dental floss may be wound onto the ring in a manner such that the dental floss is retained thereon.

The dental floss may be used in conjunction with a single ring if desired, in which the length of dental floss is cut off out of a conventional dental floss dispenser and applied to the ring, with a short length of dental floss projecting out of the slot slots. Then, further winding of dental floss can overlie the initial loop having the short length of dental floss extending sideways out of the slot, to retain the dental floss in position. Then, one may proceed with the dental flossing, with a finger placed through the ring rather than having the dental floss directly wound around the finger. As one proceeds with the flossing process, one loops the dental floss around the ring from time to time, so that new dental floss sections are exposed to the teeth.

If desired, one may also use a dental floss ring to supply the dental floss to the user, rather in the manner of unrolling movie film. Furthermore, two dental floss rings, also in the manner of movie film, may be used in which dental floss is unrolled from one ring and rolled up onto the other during the flossing process, to provide continuously new portions of the dental floss for application between the teeth.

DESCRIPTION OF SPECIFIC EMBODIMENTS

Figure 1:
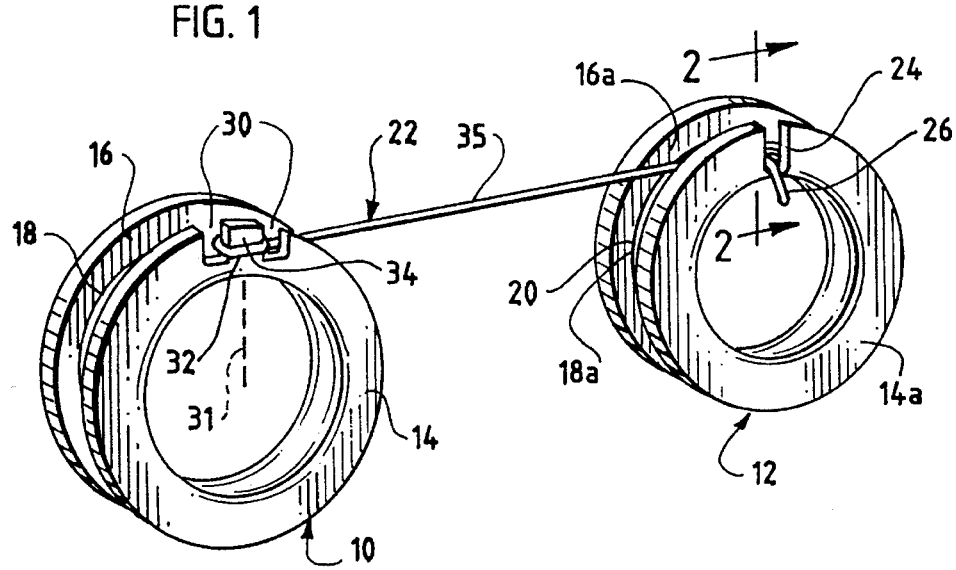
FIG. 1 is a perspective view of a pair of dental floss retainer rings of this invention, with a length of dental floss coiled on one of the rings and one end of the dental floss secured to the other.
Figure 2:
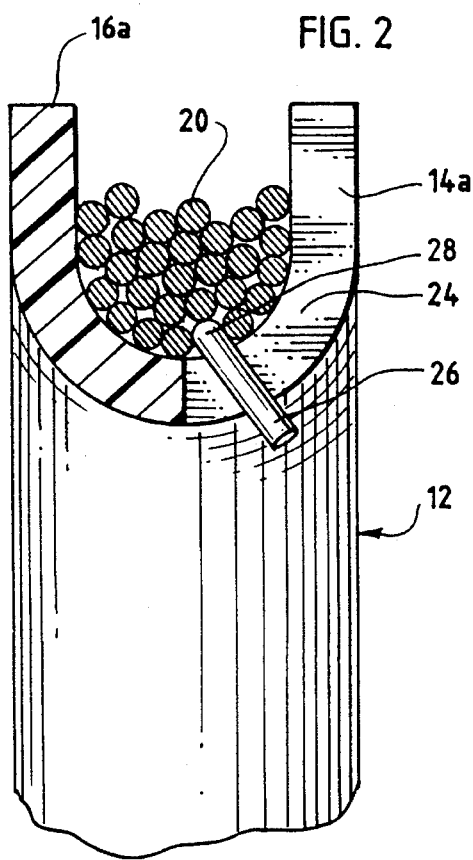
FIG. 2 is an enlarged, sectional view taken along line 2—2 of FIG. 1.

Referring to the drawings, FIGS. 1 and 2 show a pair of dental floss retainer rings 10, 12. Each of the rings 10, 12 respectively carry circumferential sidewalls 14, 16, 14a, 16a to define an external, annular space 18, 18a between the sidewalls for receiving a winding 20 of dental floss. The dental floss winding is particularly shown to be carried on ring 12, while an end length of the dental floss 22 is shown to extend from ring 12 to ring 10, and to be secured there, preparatory to winding thereon during the dental flossing process.

Retainer ring 12 defines a single, radial slot 24 in sidewall 14a, through which an end 26 of the dental floss projects in lateral manner. Because of this lateral projection, it becomes possible for subsequent windings of the dental floss to overlie the initial winding thereof 28 on ring 12, to secure the dental floss in place to facilitate the winding.

On the other hand, dental floss ring 10 comprises a different embodiment, in which a pair of parallel, substantially radial slots 30 are provided, being substantially parallel to a near by radius 31. The end length 32 of the dental floss can be wound around the post 34 that is defined between the two slots 30, to provide a different mode of connection and securance of the dental floss. If desired, post 34 may have an enlarged outer head to help retain the dental floss winding.

Both dental floss rings 10, 12 are sized to typically loosely fit on the finger of the user, without being so large that they are inconvenient in such usage. Specifically, the inner diameter of each ring 10, 12 may be about ¾ inch for adults, while smaller rings may be used for children and others with smaller fingers.

As stated above, the pair of rings 10, 12 as shown may be each typically placed on the forefinger of an opposite hand. One can then proceed with the dental flossing between a pair of teeth, using the dental floss section 35 positioned between the rings. Then, when desired, one loops a loop of dental floss about ring 10, taking the loop off of ring 12. This provides another, fresh length of dental floss between the rings which may be used for flossing, until it is desired to loop a second loop of dental floss about ring 10, taking a loop from ring 12, with this process continuing as desired throughout the flossing. Thus, when properly used the dental floss does not slip, nor is there an uncomfortable digging of the dental floss into the tissue of the fingers, as is conventional in the normal dental flossing routine. Thus, one is encouraged to do a better flossing job, and more frequently, for better tooth hygiene.

Alternatively, one can simply delete either of flossing rings 10 or 12, using the single ring typically to receive the dental floss after use and to wind it around the ring, while the other end of the dental floss is held with the fingers. Alternatively of course, one may deliver the dental floss to the user from one of the dental floss rings.

Figure 3:
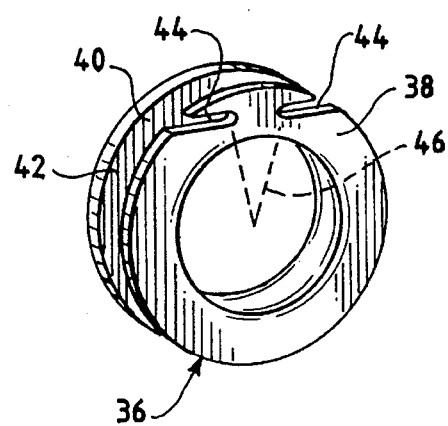
FIG. 3 is a perspective view of another embodiment of the dental floss ring of this invention.

Referring to FIG. 3, a different design of dental floss ring 36 is shown, with circumferential sidewalls 38, 40 in a manner similar to the previous embodiment to define an external, annular space 42 between the sidewalls for the winding of dental floss. In this embodiment, wall 38 is shown to carry a pair of slots 44 which extend substantially transversely to a nearest radius of the ring, examples of such nearest radii 46 being shown, i.e., radii which intersect the slots 44.

The slots of the ring of FIG. 3 also serve to retain an end of a length of dental floss, which can then be wound onto or unwound from the ring, which is held on the finger during flossing operations.

The rings of this invention are easily molded out of plastic or the like, and may be brightly colored or otherwise attractive to the user.

The above has been offered for illustrative purposes only, and is not intended to limit the scope of the invention of this application, which is as defined in the claims below.

That which is claimed is:

1. A dental floss retainer ring of an inner diameter of about ¾ inch, permitting placement on the finger and carrying a length of dental floss wound thereon, said ring defining circumferential sidewalls defining an external, annular space between said walls for receiving said length of dental floss wound about said ring, one of said walls defining at least one slot extending only incompletely across said ring to facilitate the securance of a portion of dental floss as the dental floss is wound about said ring.

2. The dental floss retainer ring of claim 1 in which one of said sidewalls defines a pair of said slots in closely spaced relation, said slots each extending substantially parallel to a nearest radius of said ring.

3. The dental floss retainer ring of claim 1 in which one of said sidewalls defines said at least one slot that extends substantially transversely to a nearest radius of said ring.

4. The dental floss retainer ring of claim 3 in which said one sidewall defines a closely spaced pair of said transversely extending slots.

5. A dental floss retainer ring of a size permitting placement on the finger and carrying a length of dental floss wound thereon, said ring defining circumferential sidewalls defining an external, annular space between said walls and carrying said length of dental floss wound about said ring, one of said walls defining a pair of slots in closely spaced relation, said slots each extending substantially parallel to a nearest radius of said ring.

6. The dental floss retainer ring of claim 5 which is made of molded plastic.

7. The method of performing dental flossing which comprises placing a winding of dental floss about a first ring which defines an external, annular space for retaining said dental floss winding; securing an end of said dental floss winding to a second dental floss retainer ring; spacing the retainer rings apart with a length of dental floss extending between them, and placing said length of dental floss between a pair of the user's teeth; winding a loop of dental floss about the second ring while removing another loop of dental floss from the first ring, to define a new section of dental floss extending between the rings, and placing said new section of dental floss through another pair of teeth of the user.

8. The method of claim 7 in which one of said rings defines circumferential sidewalls defining an external, annular space between said rings and carrying part of said dental floss wound about said ring, one of said walls defining a pair of slots in closely spaced relation, said slots each extending substantially parallel to a nearest radius of the ring.

\* \* \* \* \*